(12) United States Patent
Rasouli et al.

(10) Patent No.: US 9,656,033 B2
(45) Date of Patent: May 23, 2017

(54) HYDROSOL BASED FLAVOR DELIVERY DEVICE

(71) Applicant: PHILIP MORRIS USA INC., Richmond, VA (US)

(72) Inventors: Firooz Rasouli, Midlothian, VA (US); Wei-Jun Zhang, Richmond, VA (US); Jon Regrut, Richmond, VA (US); James Pflueger, Midlothian, VA (US)

(73) Assignee: Philip Morris USA Inc., Richmond, VA (US)

( * ) Notice: Subject to any disclaimer, the term of this patent is extended or adjusted under 35 U.S.C. 154(b) by 29 days.

(21) Appl. No.: 14/935,728

(22) Filed: Nov. 9, 2015

(65) Prior Publication Data

US 2016/0058048 A1 Mar. 3, 2016

Related U.S. Application Data

(63) Continuation of application No. 12/943,577, filed on Nov. 10, 2010, now Pat. No. 9,179,700.

(Continued)

(51) Int. Cl.
*A61M 15/06* (2006.01)
*A23P 30/40* (2016.01)
(Continued)

(52) U.S. Cl.
CPC ............. *A61M 15/06* (2013.01); *A23L 27/00* (2016.08); *A23L 27/80* (2016.08); *A23P 30/40* (2016.08);
(Continued)

(58) Field of Classification Search
CPC ......... A61M 15/06; A23P 30/40; A23L 27/00; A23L 27/80; A23V 2002/00
See application file for complete search history.

(56) References Cited

U.S. PATENT DOCUMENTS 2,704,172 A * 3/1955 Lapin ...................... B65D 83/46
215/315
3,554,771 A 1/1971 Wiczer et al.
(Continued)

FOREIGN PATENT DOCUMENTS

EP 0180483 A2 5/1986
EP 390217 A1 10/1990
(Continued)

OTHER PUBLICATIONS

International Search Report and Written Opinion mailed Feb. 23, 2011 for PCT/IB2010/002993.
(Continued)

*Primary Examiner* — Erik Kashnikow
*Assistant Examiner* — Chaim Smith
(74) *Attorney, Agent, or Firm* — Buchanan Ingersoll & Rooney PC

(57) ABSTRACT

A handheld hydrosol delivery device includes a canister which is at least partially filled with a liquid formulation of one or more liquids and optional particles, and one or more propellants where at least one of the liquids, propellants, particles and combinations thereof is a flavor; a pressure valve which expels at least a portion of the liquid formulation and at least a portion of the propellant from the canister while dispersing the propellant into the liquid formulation forming a consumable flavored hydrosol comprising one or more gases dispersed within the liquid formulation, through a nozzle delivering the hydrosol to a user.

16 Claims, 2 Drawing Sheets

Related U.S. Application Data

(60) Provisional application No. 61/259,862, filed on Nov. 10, 2009.

(51) Int. Cl.
  *A23L 27/00* (2016.01)
  *A61M 16/00* (2006.01)

(52) U.S. Cl.
  CPC .. *A23V 2002/00* (2013.01); *A61M 2016/0024* (2013.01)

(56) References Cited

U.S. PATENT DOCUMENTS

| | | | |
|---|---|---|---|
| 4,576,157 A | | 3/1986 | Raghuprasad |
| 4,765,347 A | * | 8/1988 | Sensabaugh, Jr. .... A24F 47/002 131/173 |
| 4,769,254 A | * | 9/1988 | Mays ...................... C12P 19/04 426/564 |
| 5,118,520 A | | 6/1992 | Suzuki et al. |
| 5,891,465 A | | 4/1999 | Keller et al. |
| 5,894,841 A | | 4/1999 | Voges |
| 5,906,811 A | | 5/1999 | Hersh |
| 6,005,126 A | | 12/1999 | Ishitobi et al. |
| 6,082,368 A | | 7/2000 | Brown |
| 6,623,767 B1 | | 9/2003 | Morice |
| 7,845,359 B2 | * | 12/2010 | Montaser .......... A61M 15/0085 128/200.14 |
| 2004/0118396 A1 | * | 6/2004 | Hughes ............... A61M 15/009 128/200.14 |
| 2005/0276898 A1 | | 12/2005 | Pascual et al. |
| 2008/0230052 A1 | * | 9/2008 | Montaser .......... A61M 15/0085 128/200.16 |
| 2010/0229881 A1 | | 9/2010 | Hearn |
| 2010/0310733 A1 | | 12/2010 | Hoffman |
| 2011/0041858 A1 | * | 2/2011 | Montaser .......... A61M 15/0085 131/273 |

FOREIGN PATENT DOCUMENTS

| | | |
|---|---|---|
| EP | 503767 A1 | 9/1992 |
| WO | WO 2009/001082 A1 | 12/2008 |

OTHER PUBLICATIONS

International Preliminary Report on Patentability mailed May 24, 2012 for PCT/IB2010/002993.

International Preliminary Report on Patentability mailed May 10, 2012 for PCT/EP2010//006534.

Reddi-wip Nutrition Facts, [on line] Nov. 23, 2006, retrieved on Jul. 17, 2014. Retrieved from the Internet: U RL:<http://www.dietfacts.com/htm l/nutrition-facts/reddi-wip-whipped-light-cream-original-ultra-pasteurized-sweetened-grade-a- 45962.htm>.

Buhny, reddi whip is goooooood, [on line], Nov. 20, 2004, retrieved Jul. 19, 2014. Retrieved from the Internet: URL:<https://www.flickr.com/photos/buhny/2142589/in/photostream/>.

* cited by examiner

HYDROSOL BASED FLAVOR DELIVERY DEVICE

CROSS-REFERENCE TO RELATED APPLICATIONS

This application is a continuation application of U.S. application Ser. No. 12/943,577 entitled Hydrosol Based Flavor Delivery Device, filed on Nov. 10, 2010, which claims priority under 35 U.S.C. §119(e) to U.S. Provisional Patent Application No. 61/259,862, filed Nov. 10, 2009, the entire contents of which are incorporated herein by reference.

SUMMARY

Provided is a portable handheld flavor delivery device which ejects a consumable flavored hydrosol for oral consumption comprising: one or more liquids; one or more propellants; a pressure valve that expels at least a portion of the one or more liquids and at least a portion of the one or more propellants from the portable handheld flavor delivery device while dispersing the one or more propellants into the one or more liquids, thus forming a consumable flavored hydrosol comprising one or more gases dispersed within one or more liquids, the pressure valve being activated by a pressure drop in the flavor delivery device; and a nozzle for delivery of the consumable flavored hydrosol. The pressure drop in the flavor delivery device can be created by applying a suction force to the nozzle.

DETAILED DESCRIPTION

Figure 1:
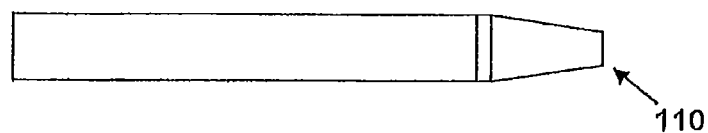
FIG. 1 shows an embodiment of a cylindrical flavor delivery device including a nozzle.

Generally, a hydrosol is a system comprising small gas bubbles dispersed within a liquid matrix. Optionally, particles can also be dispersed in the liquid, for example, flavor particles. As the gas bubbles escape from the liquid, the hydrosol can dissipate. For example, the gas bubbles can provide a carbonated fizzing effect in a user's mouth and the residual liquid and optional particles can be swallowed leaving the user with a refreshed mouth and pleasant aftertaste. In another example, the gas bubbles can be unflavored, such as air to provide a semi-solid, whipped emulsion consistency to the hydrosol.

Without wishing to be bound by theory, hydrosols are described with reference to colloidal suspensions (colloids) in terms of suspending medium and dispersed substance. A solid suspended in a liquid can be a type of colloid called a sol or a gel. Generally, sols contain individual dispersed particles and in gels the particles link together in a structure of some strength. Examples of sols and gels are protoplasm, starch, gelatin and jelly, clay and the like. Some gels can be colloids of liquid dispersed in a solid suspending medium similar to a solid emulsion, for example, cheese. When gas is dispersed in liquid the colloids are referred to as foam, such as soap suds, whipped cream and beer foam. Most foams in which the liquid phase is pure water are short lived, but if the surface tension of the water is reduced by the addition of a surface-active agent (surfactant, e.g., soap, licorice, etc.), very stable foams may be generated. Furthermore, a liquid dispersed in another liquid as suspending medium is an emulsion, such as mayonnaise (e.g., salad oil and lemon juice or vinegar in raw egg whites), milk, face cream and the like. Whipped cream is both an emulsion and a foam since both butterfat and air bubbles are colloidally suspended in the liquid. Finally, when a gas is dispersed in a solid, the colloids are referred to as solid foams, such as aerogels, polyurethane foam, etc.

The hydrosol can be produced from a formulation comprising liquid and optionally, solid elements. The formulation can be injected with gas and thoroughly mixed to produce the hydrosol and delivered to a user's mouth. Characteristics of the elements of the formulation and the degree of mixing affect the characteristics of the hydrosol. For example, when a high viscosity liquid is used to form the liquid matrix, the hydrosol behaves like a gel and may be longer lasting than a hydrosol formed with a low viscosity liquid. When a less viscous liquid is used, the hydrosol behaves more like a foam such as large gas-filled bubbles.

The formulation may comprise a combination of miscible or immiscible liquids and/or particles. Stabilizers within the liquid matrix can prolong the retention time of the gas bubbles within the liquid matrix for a long lasting foam. A surfactant in the formulation promotes the formation of the liquid matrix into the foam hydrosol. A thickener can increase the viscosity of the formulation and allow a stabile foam to form. Although a foam stabilizer is not the same as a thickener, certain elements are both thickeners and foam stabilizers.

The liquid matrix of the hydrosol may be a flavor or contain additional miscible or immiscible liquids which may be flavors. The formulation may be an emulsion of immiscible liquids. When gas is injected in the formulation to form the hydrosol, a combination of liquids can affect the texture of the resulting hydrosol.

Flavor and/or texture particles in the formulation can be dispersed throughout the formed hydrosol. The particles can be solid and remain solid or dissolve or gradually vaporize into the hydrosol gas bubbles. For example, the particles can be solids in the liquid matrix and vaporize to add a mint flavor. The particles can be a flavor such as pepper and remain solid in the formed hydrosol. The particles can be a salt which gradually dissolve in the liquid matrix of the hydrosol. Some of the particles such as mint can gradually vaporize in the hydrosol adding flavor to the small gas bubbles of the hydrosol.

The small gas bubbles can be injected into the formulation to form the hydrosol, flavor the hydrosol and propel the hydrosol. For example, the gas can comprise carbon dioxide to impart an effervescent quality to the hydrosol foam, nitrous oxide to impart a sweet flavor to the hydrosol foam or the gas can comprise air to propel the formulation and form the hydrosol while not imparting a flavor to the hydrosol.

In an exemplary embodiment, a portable handheld flavor delivery device is provided for producing a consumable flavored hydrosol for oral consumption. The consumable flavored hydrosol may be in the form of a foam. The consumable flavored hydrosol preferably contains the flavor of, for example, ginger, juniper, wintergreen, licorice, anise, cinnamon, lemon, orange, cloves, vanilla, or mixtures thereof. The consumable flavored hydrosol may contain aqueous or non-aqueous flavor compounds. The flavor compounds may comprise particles, such as, for example, menthol-containing microbeads, or menthol that has otherwise been encapsulated. Thus, the consumable flavored hydrosol allows simultaneous delivery of flavored liquid(s) with gas, which may be flavored, and optionally flavor particles. If solid particles are included, the consumable flavored hydrosol may act as a barrier to prevent small solid flavor particles from being inhaled from the mouth of a consumer into the lungs of the consumer.

The consumable flavored hydrosol may contain propylene glycol alginate, lipids, proteins (e.g., potato proteins, patatin, and/or protease inhibitors), extracts from yucca plants, foam stabilizers (e.g., Biofoam K), or mixtures thereof. Other optional consumable flavored hydrosol ingredients include surfactants (for lowering the surface tension of the liquid) and thickening agents. When the consumable flavored hydrosol does not contain any thickening agents, the resulting hydrosol may resemble bubbles which are preferably stable and less dense than a foam formed with thickening agents. The formulation of the consumable flavored hydrosol may be adjusted (e.g., by changing the proportions of the disclosed ingredients and/or including additional ingredients) such that the resulting hydrosol more closely resembles a gel than a foam.

Figure 2:
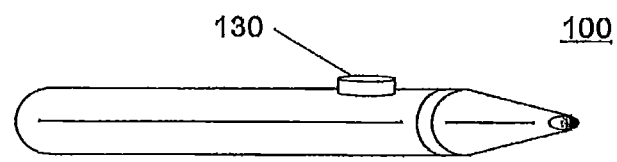
FIG. 2 shows another embodiment of a cylindrical flavor delivery device including a manual input.
Figure 3:
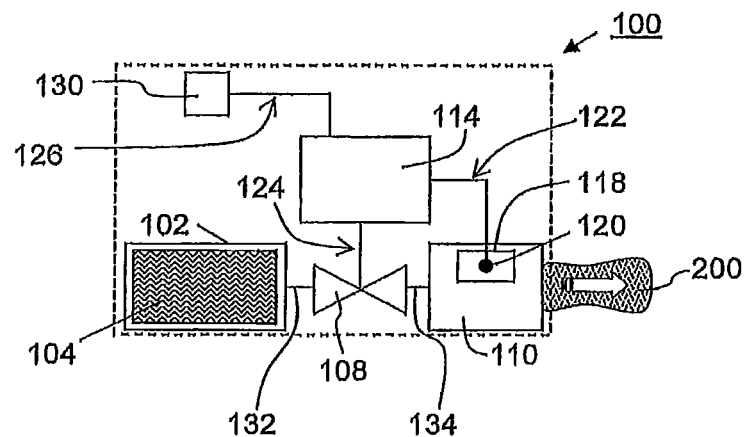
FIG. 3 illustrates an embodiment of a consumable flavored hydrosol delivery device.

FIG. 1 shows an embodiment of a cylindrical flavor delivery device 100 including a nozzle 110 (mouthpiece or constriction to increase the dispersion of the gas into the liquid by shearing the gas bubbles into smaller sized gas bubbles or by more uniformly dispersing the gas bubbles in the liquid). FIG. 2 shows another embodiment of a cylindrical flavor delivery device including an optional manual input 130. FIG. 3 shows a schematic of an exemplary embodiment of the flavor delivery device 100. The flavor delivery device 100 comprises one or more liquids, one or more propellants and optionally, one or more particles in a canister 102. For example, the liquids, propellants and particles may be a formulation 104 under pressure in the canister 102. Optionally, these elements of the formulation may be stored in separate canisters (not shown) to be combined only at the time of hydrosol formation.

According to the embodiment shown in FIG. 3, a pressure valve 108 expels at least a portion of the one or more liquids, at least a portion of the one or more propellants and optionally, at least a portion of the one or more particles from the portable handheld flavor delivery device 100 canister 102. Preferably, the one or more propellants are dispersed into the one or more liquids as they exit the canister 102 forming the consumable flavored hydrosol 200 comprising one or more gases dispersed within the one or more liquids with the optional particles.

The pressure valve 108 can be activated automatically or manually. Preferably, manual operation, for example manual input resulting in the depression of a bias spring of the pressure valve 108, delivers the consumable flavored hydrosol 200 to a consumers mouth (not shown). Also preferably, a controller 114 receives a flow signal from a flow sensor 120 located in the nozzle (mouthpiece) 110 of the flavor delivery device 100 when a consumer induces a pressure drop in the nozzle 110 or an activation signal from an optional manual input 130. For example, air flowing past a flow opening 118 in the nozzle 110 can be sensed by the flow sensor 120 which sends the flow signal to the controller 114 over transmit line 122. In response to the flow signal the controller 114 sends a valve signal over transmit line 124 to pressure valve 108 activating the pressure valve 108 to deliver the consumable flavored hydrosol 200 to a consumer's mouth. Optional flow passages 132 and 134 can provide a delivery route from the canister 102 to the nozzle 110 via the pressure valve 108. In another example, the consumer can activate a manual input 130, such as pressing a button or rotating a knob, to send the activation signal to the controller 114 over transmit line 126. In response to the activation signal, the controller 114 sends the valve signal over transmit line 124 to pressure valve 108 activating the pressure valve 108 to deliver the consumable flavored hydrosol 200 to the consumer's mouth. The signal transmit lines 122/124/126 are not particularly limited and can be wired or wireless.

The pressure valve 108 can comprise a sensor that detects a pressure drop in the flavor delivery device 100 and control circuitry that activates the pressure valve 108. In particular, the pressure sensor can be in (fluid) communication with the nozzle 110 via a flow passage 134. The flow passage 134 can include a flow opening through which ambient air can be drawn into the flow passage 134 by a user applying suction to the nozzle 110. Thus, the flavor delivery device 100 can be activated by a user inhaling or applying suction on an outlet of the nozzle 110. This application of suction causes a differential pressure in the flow passage 134, which is sensed by the sensor 120. The sensor 120 can be extremely sensitive. For example, the sensor 120 can be triggered at a selected threshold value of air flow through the passage, for example, as low as about 3 liters/min. This value equals less than about $1/10$ of the typical human inhalation flow rate. Accordingly, the user can trigger the flow sensor 120 without wasting appreciable lung volume. Stated otherwise, when a user inhales on the nozzle 110, the pressure drop in the nozzle 110 is sensed by the sensor 120. Upon detection of the pressure drop by the sensor 120, the sensor 120 sends a signal to control circuitry, which causes activation of the pressure valve 108.

Figure 4:
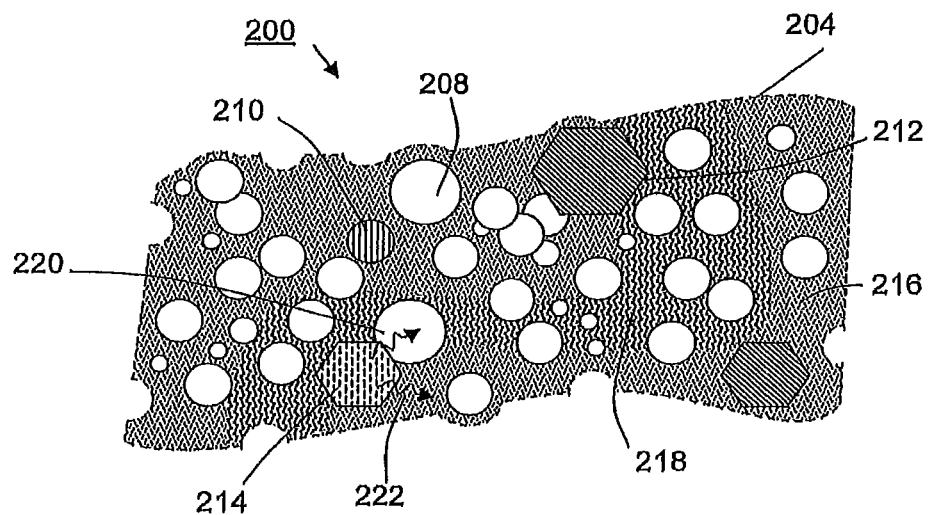
FIG. 4 shows an embodiment of a consumable flavored hydrosol.

FIG. 4 shows an exemplary embodiment of a consumable flavored hydrosol 200 produced by the flavor delivery device 100. The flavored hydrosol 200 comprises a consumable flavored hydrosol matrix 204 comprising a first liquid 216 and a second liquid 218. As illustrated in FIG. 4, the second liquid 218 may be embedded in the first liquid 216 as discrete swirls (regions) of contrasting color and flavor. First gas bubbles 208 and second gas bubbles 210 are shown in the flavored hydrosol 200 surrounded by the liquid matrix 204. First particles 212 and second particles 214 are shown dispersed in the liquid matrix 204 of the flavored hydrosol. FIG. 4 illustrates the second particles 214 vaporizing into the first gas bubbles at arrow 220 and dissolving in first liquid 216 at arrow 222.

At least a portion of the one or more liquids may be pressurized in the canister 102. At least a portion of the one or more propellants may be a propellant gas, a compressed gas, or a liquid that forms a gas when expelled from the pressure valve 108 of the portable handheld flavor delivery device 100 while being dispersed into the one or more liquids. The one or more propellants may comprise carbon dioxide. The carbon dioxide may aid in pressurizing at least a portion of the one or more liquids. Carbon dioxide may provide additional flavor, effervescence or carbonation to the formed consumable flavored hydrosol 200.

Also provided is a method of producing a consumable flavored hydrosol 200 to a consumer's mouth. An embodiment of the method comprises providing a portable handheld flavor delivery device 100 comprising one or more liquids, one or more propellants, optional particles, a pressure valve 108, and a nozzle 110; and creating a pressure drop in the flavor delivery device 100 by puffing on the nozzle 110, which activates the pressure valve 108. The pressure drop expels at least a portion of the one or more liquids, at least a portion of the one or more propellants and optional particles from the portable handheld flavor delivery device 100. Preferably, the one or more propellants are dispersed into the one or more liquids as they exit the canister 102, thus forming a consumable flavored hydrosol 200 comprising one or more gases (e.g., the first gas 208 and second gas 210) dispersed within one or more liquids (e.g., the first liquid 216 and second liquid 218) containing optional particles (e.g., first particles 212 and second particles 214), which is delivered for oral consumption, e.g., to the consumer's mouth, through the nozzle 110.

In another embodiment of producing a consumable flavored hydrosol 200 for oral consumption, the method includes providing a portable handheld flavor delivery device 100 comprising one or more liquids, one or more gases, optional particles, a pressure valve 108, and a nozzle 110; and manually activating the pressure valve 108. The activated pressure valve 108 expels at least a portion of the one or more liquids and at least a portion of the one or more gases from the portable handheld flavor delivery device 100 while dispersing the one or more gases into the one or more liquids having optional particles. The dispersed gases in the liquids thus forming a consumable flavored hydrosol 200 comprising one or more gases and optional particles dispersed within one or more liquids, which is delivered for oral consumption, e.g., to the consumer's mouth, through the nozzle 110.

While various embodiments have been described, it is to be understood that variations and modifications may be resorted to as will be apparent to those skilled in the art. Such variations and modifications are to be considered within the purview and scope of the claims appended hereto.

What is claimed is:

1. A method of producing a consumable flavored hydrosol for oral consumption with a portable handheld flavor delivery device, the portable handheld flavor delivery device comprising at least one canister therein wherein the at least one canister includes one or more liquids and one or more propellants, the method comprising:
    expelling at least a portion of the one or more liquids and at least a portion of the one or more propellants from the at least one canister while dispersing the one or more propellants into the one or more liquids so as to form a consumable flavored hydrosol comprising one or more gases mixed within one or more liquids;
    wherein the portable handheld flavor delivery device includes a pressure valve that is activated via a pressure drop such that the one or more propellants and the one or more liquids are expelled from the pressure valve when the pressure valve is activated.

2. The method of claim 1, wherein the portable handheld device comprises a nozzle, the method comprising applying a suction force to the nozzle to activate the pressure valve.

3. The method of claim 1, wherein the portable handheld device includes a flow sensor and a controller, the method further comprising sensing air flow created by a pressure drop with the flow sensor, sending a signal to the controller from the flow sensor when airflow is sensed, and activating the pressure valve by sending a signal from the controller to the pressure valve.

4. The method of claim 1, wherein the at least one canister comprises a first canister and a second canister, the method comprising expelling the one or more propellants from the first canister and expelling the one or more liquids from the second canister.

5. The method of claim 1, wherein the portable handheld device comprises a nozzle, the method further comprising delivering the consumable flavored hydrosol through the nozzle to a consumer's mouth.

6. The method of claim 1, comprising pressurizing a portion of the one or more liquids before expelling the one or more liquids.

7. The method of claim 1, wherein at least a portion of the one or more propellants comprises a compressed gas.

8. The method of claim 1, wherein at least a portion of the one or more propellants comprises a liquid that forms a gas when expelled wherein the liquid that forms a gas when expelled is dispersed into the one or more liquids.

9. The method of claim 1, wherein the one or more liquids comprises one or more thickening agents such that the consumable flavored hydrosol comprises one or more thickening agents.

10. The method of claim 1, wherein the one or more propellants comprises one of carbon dioxide, oxygen, nitrous oxide, air or a combination thereof.

11. The method of claim 1, wherein the consumable flavored hydrosol comprises one or more flavor compounds, and further wherein the one or more liquids optionally comprise the one or more flavor compounds; and
    (a) the one or more flavor compounds comprise one or more non-aqueous flavor compounds; and/or
    (b) the one or more flavor compounds comprise one or more aqueous flavor compounds.

12. The method of claim 1, wherein
    (a) the consumable flavored hydrosol comprises one or more surfactants, and further wherein the one or more liquids optionally comprise the one or more surfactants;
    (b) the consumable flavored hydrosol comprises one or more ingredients selected from the group consisting of propylene glycol alginate, lipids, proteins, extracts from yucca plants, foam stabilizers, and mixtures thereof;
    (c) the consumable flavored hydrosol comprises one or more particles, and further wherein the one or more liquids comprise the one or more particles; and/or
    (d) the consumable flavored hydrosol comprises a foam, a gel, an emulsion or a combination thereof.

13. The method of claim 1, wherein the consumable flavored hydrosol comprises a flavor selected from the group consisting of ginger, juniper, wintergreen, licorice, anise, cinnamon, lemon, orange, cloves, vanilla, menthol and mixtures thereof.

14. The method of claim 1, further comprising expelling one or more particles with the one or more liquids and the one or more propellants and dispersing the one or more particles with the one or more propellants into the one or more liquids, thus forming a consumable flavored hydrosol comprising one or more gases and one or more particles dispersed within one or more liquids.

15. The method of claim 14, wherein the particles are solids that vaporize in the hydrosol wherein the particles add flavor to the consumable flavored hydrosol.

16. The method of claim 14, wherein the particles are a salt that dissolves in a liquid matrix of the consumable flavored hydrosol.

* * * * *